(12) United States Patent
Belko et al.

(10) Patent No.: US 9,029,535 B2
(45) Date of Patent: *May 12, 2015

(54) PYRIMIDINE DERIVATIVES AND THEIR USE IN PERFUME COMPOSITIONS

(71) Applicant: International Flavors & Fragrances Inc., New York, NY (US)

(72) Inventors: Robert P. Belko, Monroe, NJ (US); Paul D. Jones, Aberdeen, NJ (US); Anthony T. Levorse, Jr., Westfield, NJ (US); Michael G. Monteleone, Hazlet, NJ (US); Anubhav P. S. Narula, Hazlet, NJ (US); Franc T. Schiet, Naarden (NL)

(73) Assignee: International Flavors & Fragrances Inc., New York, NY (US)

(*) Notice: Subject to any disclaimer, the term of this patent is extended or adjusted under 35 U.S.C. 154(b) by 22 days.

This patent is subject to a terminal disclaimer.

(21) Appl. No.: 13/974,023

(22) Filed: Aug. 22, 2013

(65) Prior Publication Data

US 2015/0057206 A1 Feb. 26, 2015

Related U.S. Application Data

(63) Continuation-in-part of application No. 13/540,894, filed on Jul. 3, 2012, now Pat. No. 8,557,876, which is a continuation-in-part of application No. 13/430,908, filed on Mar. 27, 2012, now Pat. No. 8,557,827, which is a continuation-in-part of application No. 13/027,314, filed on Feb. 15, 2011, now Pat. No. 8,709,993.

(51) Int. Cl.
C07D 239/70 (2006.01)
C11B 9/00 (2006.01)
C11D 3/50 (2006.01)

(52) U.S. Cl.
CPC .............. *C11B 9/0092* (2013.01); *C11D 3/50* (2013.01); *C07D 239/70* (2013.01)

(58) Field of Classification Search
CPC ..................................................... C07D 239/70
USPC ............................................. 544/249; 512/10
See application file for complete search history.

(56) References Cited

U.S. PATENT DOCUMENTS 7,713,966 B2 * 5/2010 Gege et al. ................. 514/230.5
2010/0204226 A1 * 8/2010 Bembenek et al. ........ 514/234.5

* cited by examiner

*Primary Examiner* — John Hardee
(74) *Attorney, Agent, or Firm* — XuFan Tseng; Zhijun Zhang; Elizabeth M. Quirk

(57) ABSTRACT

The present invention relates to novel pyrimidine derivatives and their use in perfume compositions. The novel pyrimidine derivatives of the present invention are represented by the following formula:

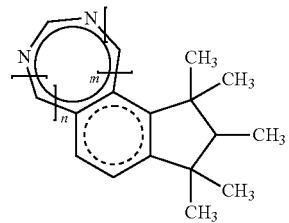

wherein m and n are integers of 0 or 1, with the proviso that when m is 0, n is 1 and when m is 1, n is 0; and
wherein the dashed circle represents either single or double bonds.

17 Claims, No Drawings

PYRIMIDINE DERIVATIVES AND THEIR USE IN PERFUME COMPOSITIONS

STATUS OF RELATED APPLICATIONS

This application is a continuation-in-part of U.S. Ser. No. 13/027,314, filed Feb. 15, 2011, now issued into U.S. Pat. No. 8,709,993. This application is also a continuation-in-part of U.S. Ser. No. 13/540,894, filed Jul. 3, 2012, now issued into U.S. Pat. No. 8,557,876, which is a continuation-in-part of U.S. Ser. No. 13/430,908, filed Mar. 27, 2012, now issued into U.S. Pat. No. 8,557,827, which is a continuation-in-part of U.S. Ser. No. 13/027,314, filed Feb. 15, 2011, now issued into U.S. Pat. No. 8,709,993, the contents hereby incorporated by reference as if set forth in its entirety.

FIELD OF THE INVENTION

The present invention relates to new chemical entities and the incorporation and use of the new chemical entities as fragrance materials.

BACKGROUND OF THE INVENTION

There is an ongoing need in the fragrance industry to provide new chemicals to give perfumers and other persons the ability to create new fragrances for perfumes, colognes and personal care products. Those with skill in the art appreciate how differences in the chemical structure of the molecule can result in significant differences in the odor, notes and characteristics of a molecule. These variations and the ongoing need to discover and use the new chemicals in the development of new fragrances allow the perfumers to apply the new compounds in creating new fragrances.

SUMMARY OF THE INVENTION

The present invention provides novel compounds and their unexpected advantageous use in enhancing, improving or modifying the fragrance of perfumes, colognes, toilet water, fabric care products, personal products and the like.

More specifically, the present invention relates to pyrimidine derivatives represented by Formula I set forth below:

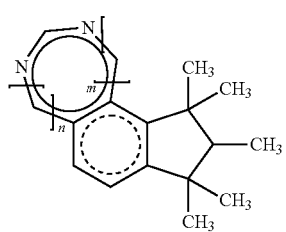

Formula I wherein m and n are integers of 0 or 1 with the proviso that when m is 0, n is 1 and when m is 1, n is 0; and wherein the dashed circle represents either single or double bonds.

Another embodiment of the present invention relates to pyrimidine derivatives represented by Formula II set forth below:

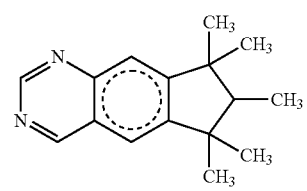

Formula II wherein the dashed circle represents either single or double bonds.

Another embodiment of the present invention relates to a fragrance composition comprising the novel compounds provided above.

Another embodiment of the present invention relates to a fragrance product comprising the compounds provided above.

Another embodiment of the present invention relates to a method of improving, enhancing or modifying a fragrance formulation through the addition of an olfactory acceptable amount of the novel compounds provided above.

These and other embodiments of the present invention will be apparent by reading the following specification.

DETAILED DESCRIPTION OF THE INVENTION

The compounds of the present invention may be represented by the following structures:

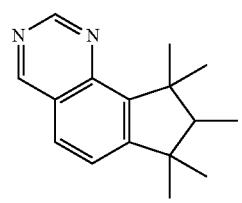

Formula III

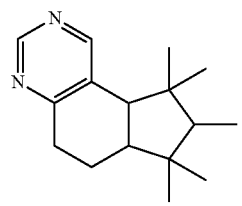

Formula IV

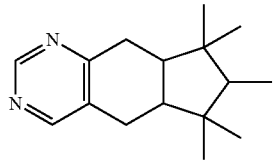

Formula V

Those with the skill in the art will appreciate that

Formula III is 7,7,8,9,9-pentamethyl-8,9-dihydro-7H-cyclopenta[H]quinazoline;

Formula IV is 7,7,8,9,9-pentamethyl-6,6A,7,8,9,9A-hexahydro-5H-cyclopenta(F)quinazoline; and Formula V is 6,6,7,8,8-pentamethyl-5A,6,7,8,8A,9-hexahydro-5H-cyclopenta(G)quinazoline.

Those with skill in the art will recognize that the compounds of the present invention contain chiral centers, thereby providing a number of isomers of the claimed compounds. It is intended herein that the compounds described herein include isomeric mixtures of such compounds, as well as those isomers that may be separated using techniques known to those having skill in the art. Suitable techniques include chromatography such as high performance liquid chromatography, referred to as HPLC, and particularly silica gel chromatography and gas chromatography trapping known as GC trapping. Yet, commercial products are mostly offered as isomeric mixtures.

The preparation of the compounds of the present invention is detailed in the Examples. Materials were purchased from Aldrich Chemical Company unless noted otherwise.

The use of the compounds of the present invention is widely applicable in current perfumery products, including the preparation of perfumes and colognes, the perfuming of personal care products such as soaps, shower gels, and hair care products, fabric care products, air fresheners, and cosmetic preparations. The present invention can also be used to perfume cleaning agents, such as, but not limited to detergents, dishwashing materials, scrubbing compositions, window cleaners and the like.

In these preparations, the compounds of the present invention can be used alone or in combination with other perfuming compositions, solvents, adjuvants and the like. The nature and variety of the other ingredients that can also be employed are known to those with skill in the art. Many types of fragrances can be employed in the present invention, the only limitation being the compatibility with the other components being employed. Suitable fragrances include but are not limited to fruits such as almond, apple, cherry, grape, pear, pineapple, orange, strawberry, raspberry; musk, flower scents such as lavender-like, rose-like, iris-like, carnation-like. Other pleasant scents include herbal and woodland scents derived from pine, spruce and other forest smells. Fragrances may also be derived from various oils, such as essential oils, or from plant materials such as peppermint, spearmint and the like.

A list of suitable fragrances is provided in U.S. Pat. No. 4,534,891, the contents of which are incorporated by reference as if set forth in its entirety. Another source of suitable fragrances is found in *Perfumes, Cosmetics and Soaps*, Second Edition, edited by W. A. Poucher, 1959. Among the fragrances provided in this treatise are acacia, cassie, chypre, cyclamen, fern, gardenia, hawthorn, heliotrope, honeysuckle, hyacinth, jasmine, lilac, lily, magnolia, mimosa, narcissus, freshly-cut hay, orange blossom, orchid, reseda, sweet pea, trefle, tuberose, vanilla, violet, wallflower, and the like.

The compounds of the present invention can be used in combination with a complementary fragrance compound. The term "complementary fragrance compound" as used herein is defined as a fragrance compound selected from the group consisting of 2-[(4-methylphenyl)methylene]-heptanal (Acalea), iso-amyl oxyacetic acid allylester (Allyl Amyl Glycolate), (3,3-dimethylcyclohexyl)ethyl ethyl propane-1,3-dioate (Applelide), (E/Z)-1-ethoxy-1-decene (Arctical), 2-ethyl-4-(2,2,3-trimethyl-3-cyclo-penten-1-yl)-2-buten-1-ol (Bacdanol), 2-methyl-3-[(1,7,7-trimethylbicyclo[2.2.1]hept-2-yl)oxy]exo-1-propanol (Bornafix), 1,2,3,5,6,7-hexahydro-1,1,2,3,3-pentamethyl-4H-inden-4-one (Cashmeran), trimethylcyclopentenylmethyloxabicyclooctane (Cassiffix), 1,1-dimethoxy-3,7-dimethyl-2,6-octadiene (Citral DMA), 3,7-dimethyl-6-octen-1-ol (Citronellol), 3A,4,5,6,7,7A-hexahydro-4,7-methano-1H-inden-5/6-yl acetate (Cyclacet), 3A,4,5,6,7,7A-hexahydro-4,7-methano-1H-inden-5/6-yl propinoate (Cycloprop), 3A,4,5,6,7,7A-hexahydro-4,7-methano-1G-inden-5/6-yl butyrate (Cyclobutanate), 1-(2,6,6-trimethyl-3-cyclohexen-1-yl)-2-buten-1-one (Delta Damascone), 3-(4-ethylphenyl)-2,2-dimethyl propanenitrile (Fleuranil), 3-(O/P-ethylphenyl) 2,2-dimethyl propionaldehyde (Floralozone), tetrahydro-4-methyl-2-(2-methylpropyl)-2H-pyran-4-ol (Floriffol), 1,3,4,6,7,8-hexahydro-4,6,6,7,8,8-hexamethylcyclopenta-gamma-2-benzopyran (Galaxolide), 1-(5,5-dimethyl-1-cyclohexen-1-yl)pent-4-en-1-one (Galbascone), E/Z-3,7-dimethyl-2,6-octadien-1-yl acetate (Geranyl Acetate), α-methyl-1,3-benzodioxole-5-propanal (Helional), 1-(2,6,6-trimethyl-2-cyclohexen-1-yl)-1,6-heptadien-3-one (Hexylon), (Z)-3-hexenyl-2-hydroxybenzoate (Hexenyl Salicylate, CIS-3), 4-(2,6,6-trimethyl-2-cyclohexen-1-yl)-3-buten-2-one (Ionone α), 1-(1,2,3,4,5,6,7,8-octahydro-2,3,8,8-tetramethyl-2-naphthalenyl)-ethan-1-one (Iso E Super), methyl 3-oxo-2-pentylcyclopentaneacetate (Kharismal), 2,2,4-trimethyl-4-phenyl-butanenitrile (Khusinil), 3,4,5,6,6-pentamethylhept-3-en-2-one (Koavone), 3/4-(4-hydroxy-4-methylpentyl)cyclohexene-1-carboxaldehyde (Lyral), 3-methyl-4-(2,6,6-trimethyl-2-cyclohexen-1-yl)-3-buten-2-one (Methyl Ionone γ), 1-(2,6,6-trimethyl-2-cyclohexen-1-yl) pent-1-en-3-one (Methyl Ionone α Extra, Methyl Ionone N), 3-methyl-4-phenylbutan-2-ol (Muguesia), cyclopentadec-4-en-1-one (Musk Z4), 3,3,4,5,5-pentamethyl-11,13-dioxatricyclo[7.4.0.0<2,6>]tridec-2(6)-ene (Nebulone), 3,7-dimethyl-2,6-octadien-1-yl acetate (Neryl Acetate), 3,7-dimethyl-1,3,6-octatriene (Ocimene), ortho-tolylethanol (Peomosa), 3-methyl-5-phenylpentanol (Phenoxanol), 1-methyl-4-(4-methyl-3-pentenyl)cyclohex-3-ene-1-carboxaldehyde (Precyclemone B), 4-methyl-8-methylene-2-adamantanol (Prismantol), 2-ethyl-4-(2,2,3-trimethyl-3-cyclopenten-1-yl)-2-buten-1-ol (Sanjinol), 2-methyl-4-(2,2,3-trimethyl-3-cyclopenten-1-yl)-2-buten-1-ol (Santaliff), Terpineol, 2,4-dimethyl-3-cyclohexene-1-carboxaldehyde (Triplal), decahydro-2,6,6,7,8,8-hexamethyl-2H-indeno[4,5-B]furan (Trisamber), 2-tert-butylcyclohexyl acetate (Verdox), 4-tert-butylcyclohexyL acetate (Vertenex), acetyl cedrene (Vertofix), 3,6/4,6-dimethylcyclohex-3-ene-1-carboxaldehyde (Vertoliff), and (3Z)-1-[(2-methyl-2-propenyl)oxy]-3-hexene (Vivaldie).

The terms "fragrance formulation", "fragrance composition", and "perfume composition" mean the same and refer to a consumer composition that is a mixture of compounds including, for example, alcohols, aldehydes, ketones, esters, ethers, lactones, nitriles, natural oils, synthetic oils, and mercaptans, which are admixed so that the combined odors of the individual components produce a pleasant or desired fragrance. The fragrance formulation of the present invention is a consumer composition comprising a compound of the present invention. The fragrance formulation of the present invention comprises a compound of the present invention and further a complementary fragrance compound as defined above.

The term "fragrance product" means a consumer product that adds a fragrance or masks a malodor. Fragrance products may include, for example, perfumes, colognes, personal care products such as soaps, shower gels, and hair care products, fabric products, air fresheners, cosmetic preparations, and perfume cleaning agents such as detergents, dishwashing materials, scrubbing compositions, and window cleaners. The fragrance product of the present invention is a consumer product that contains a compound of the present invention. The fragrance product of the present invention contains a compound of the present invention and further a complementary fragrance compound as defined above.

The term "improving" in the phrase "improving, enhancing or modifying a fragrance formulation" is understood to mean raising the fragrance formulation to a more desirable character. The term "enhancing" is understood to mean making the fragrance formulation greater in effectiveness or providing the fragrance formulation with an improved character.

The term "modifying" is understood to mean providing the fragrance formulation with a change in character.

The term "olfactory acceptable amount" is understood to mean the amount of a compound in a fragrance formulation, wherein the compound will contribute its individual olfactory characteristics. However, the olfactory effect of the fragrance formulation will be the sum of effect of each of the fragrance ingredients. Thus, the compound of the present invention can be used to improve or enhance the aroma characteristics of the fragrance formulation, or by modifying the olfactory reaction contributed by other ingredients in the formulation. The olfactory acceptable amount may vary depending on many factors including other ingredients, their relative amounts and the olfactory effect that is desired.

The amount of the compounds of the present invention employed in a fragrance formulation varies from about 0.005 to about 70 weight percent, preferably from 0.005 to about 50 weight percent, more preferably from about 0.5 to about 25 weight percent, and even more preferably from about 1 to about 10 weight percent. Those with skill in the art will be able to employ the desired amount to provide desired fragrance effect and intensity. In addition to the compounds of the present invention, other materials can also be used in conjunction with the fragrance formulation. Well known materials such as surfactants, emulsifiers, polymers to encapsulate the fragrance can also be employed without departing from the scope of the present invention.

When used in a fragrance formulation these ingredients provide additional notes to make a fragrance formulation more desirable and noticeable, and add the perception of value. The odor qualities found in these materials assist in beautifying and enhancing the finished accord as well as improving the performance of the other materials in the fragrance.

The following are provided as specific embodiments of the present invention. Other modifications of this invention will be readily apparent to those skilled in the art. Such modifications are understood to be within the scope of this invention. As used herein all percentages are weight percent unless otherwise noted, ppm is understood to stand for parts per million, L is understood to be liter, mL is understood to be milliliter, g is understood to be gram, Kg is understood to be kilogram, and mmHg be millimeters (mm) of mercury (Hg). IFF as used in the examples is understood to mean International Flavors & Fragrances Inc., New York, N.Y., USA.

Example I

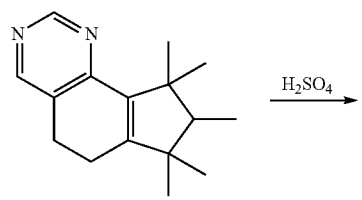

7,7,8,9,9-pentamethyl-6,7,8,9-
tetrahydro-5H-cyclopental[H]
quinazoline

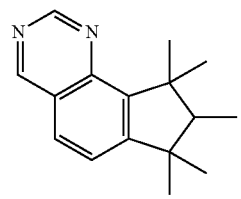 [SMILES: CC1C(C)(C)c2ccc3cncnc3c2C1(C)C]

Formula III

Preparation of 7,7,8,9,9-Pentamethyl-8,9-dihydro-
7H-cyclopenta[H]quinazoline (Formula III)

7,7,8,9,9-Pentamethyl-6,7,8,9-tetrahydro-5H-cyclopenta [H]quinazoline was prepared as described in EXAMPLE I of U.S. Publication No. 2012/0207697 and in EXAMPLE I of U.S. Publication No. 2012/0277325. A 3-L reaction vessel was charged with 7,7,8,9,9-pentamethyl-6,7,8,9-tetrahydro-5H-cyclopenta[H]quinazoline (1 Kg) and sulfuric acid ($H_2SO_4$) (100 g). The reaction mixture was heated to 220° C. for 12 hours and then cooled to 80° C. The resulting mixture was diluted with toluene (1 L). The organic layer was separated and washed twice with brine (2 L), twice with aqueous sodium hydroxide (NaOH) (25%, 2 L) and then twice with brine (2 L). The crude product was purified by vacuum distillation to afford 7,7,8,9,9-Pentamethyl-8,9-dihydro-7H-cyclopenta[H]quinazoline (992 g) having a boiling point of 160° C. at 1.0 mmHg. Further recrystallization from ethanol afforded a solid with a melting point of 84.0° C.

$^1$HNMR ($CDCl_3$, 500 MHz): 9.30 ppm (s, 1H), 9.29 ppm (s, 1H), 7.74 ppm (d, 1H, J=8.28 Hz), 7.47 ppm (d, 1H, J=8.28 Hz), 2.02 ppm (q, 1H, J=7.36 Hz), 1.74 ppm (s, 3H), 1.39 ppm (s, 3H), 1.37 ppm (s, 3H), 1.10 ppm (s, 3H), 1.06 ppm (d, 3H, J=7.36 Hz), 7,7,8,9,9-Pentamethyl-8,9-dihydro-7H-cyclopenta[H] quinazoline was described as having musky, creamy, sweet and warm notes.

Example II

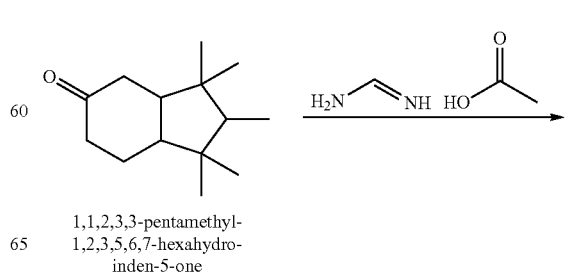

1,1,2,3,3-pentamethyl-
1,2,3,5,6,7-hexahydro-
inden-5-one

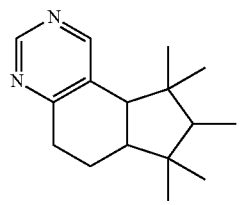 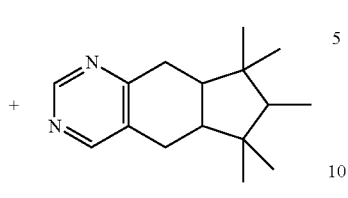

Formula IV    Formula V

Preparation of 7,7,8,9,9-Pentamethyl-6,6A,7,8,9,9A-hexahydro-5H-cyclopenta(F)quinazoline (Formula IV) and 6,6,7,8,8-Pentamethyl-5A,6,7,8,8A,9-hexahydro-5H-cyclopenta(G)quinazoline (Formula V)

A 100 mL reaction flask was charged with 1,1,2,3,3-pentamethyl-1,2,3,5,6,7-hexahydro-inden-5-one (10 g) (prepared as described in U.S. Pat. No. 3,767,713), formamidine acetate (HN=CHNH$_2$.CH$_3$COOH) (25 g) and butanol (C$_4$H$_9$OH) (120 mL). Boron triflouride (BF$_3$) (3 g) was added. The reaction mixture was then heated to 140° C. and stirred for 3 hours. The crude mass was washed once with aqueous sulfuric acid (H$_2$SO$_4$) (10%, 100 mL) followed by twice with brine (30 mL). Butanol was recovered by roto-evaporation. The crude product was further purified with liquid chromatography followed by crystallization to afford a mixture of 7,7,8,9,9-Pentamethyl-6,6A,7,8,9,9A-hexahydro-5H-cyclopenta(F)quinazoline (Formula IV) and 6,6,7,8,8-Pentamethyl-5A,6,7,8,8A,9-hexahydro-5H-cyclopenta(G) quinazoline (Formula V) in a ratio of about 1:1 (1.1 g). Products were separated and confirmed by NMR analysis with GC trapping. 7,7,8,9,9-Pentamethyl-6,6A,7,8,9,9A-hexahydro-5H-cyclopenta(F)quinazo line:

$^1$H NMR (CDCl$_3$, 500 MHz): 8.92 ppm (s, 1H), 8.64 ppm (s, 1H), 2.99 ppm (d, 1H, J=8.51 Hz), 2.91-2.99 ppm (m, 2H), 2.05-2.13 ppm (m, 1H), 1.89-1.96 ppm (m, 1H), 1.65-1.78 ppm (m, 1H), 1.60 ppm (q, 1H, J=7.0 Hz), 1.22 ppm (s, 3H), 1.11 ppm (s, 3H), 0.85 ppm (d, 3H, J=7.0 Hz), 0.94 ppm (s, 3H), 0.54 ppm (s, 3H)

7,7,8,9,9-Pentamethyl-6,6A,7,8,9,9A-hexahydro-5H-cyclopenta(F)quinazoline was described as having ambery, musky and fruity notes.

6,6,7,8,8-Pentamethyl-5A,6,7,8,8A,9-hexahydro-5H-cyclopenta(G)quinazoline:

$^1$H NMR (CDCl$_3$, 500 MHz): 8.93 ppm (s, 1H), 8.37 ppm (s, 1H), 2.85 ppm (d, 1H, J=15.0 Hz, of d, J=6.46 Hz), 2.61-2.73 ppm (m, 2H), 2.48 ppm (d, 1H, J=14.7 Hz, of d, J=11.50 Hz), 1.97-2.10 ppm (m, 2H), 1.54 ppm (q, 1H, J=7.27 Hz), 1.03 ppm (s, 3H), 1.01 ppm (s, 3H), 0.88 ppm (s, 3H), 0.87 ppm (d, 3H, J=7.27 Hz), 0.86 ppm (s, 3H)

6,6,7,8,8-Pentamethyl-5A,6,7,8,8A,9-hexahydro-5H-cyclopenta(G)quinazoline was described as having ambery, musky and fruity notes.

Example III

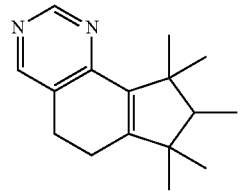 [SMILES: CC1C(C)(C)C2=C(c3ncncc3CC2)C1(C)C]

Formula VI

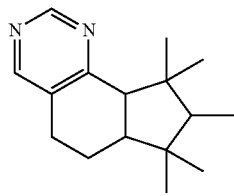 [SMILES: CC1C(C)(C)C2CCc3cncnc3C2C1(C)C]

Formula VII

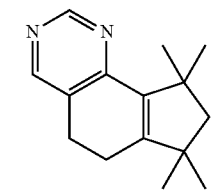 [SMILES: CC1(C)CC(C)(C)C2=C1CCc1cncnc12]

Formula VIII

Preparation of 6,7,8,9-Tetrahydro-7,7,8,9,9-pentamethyl-5H-cyclopenta[H]quinazoline (Formula VI), 6,6a,7,8,9,9a-Hexahydro-7,7,8,9,9-pentamethyl-5H-cyclopenta[H]quinazoline (Formula VII) and 1,1,3,3-Tetramethyl-2,3,4,5-tetrahydro-1H-7,9-diaza-cyclopenta[a]naphthalene (Formula VIII)

6,7,8,9-Tetrahydro-7,7,8,9,9-pentamethyl-5H-cyclopenta[H]quinazoline (Formula VI) and 6,6a,7,8,9,9a-hexahydro-7,7,8,9,9-pentamethyl-5H-cyclopenta[H]quinazoline (Formula VII) were prepared according to the disclosure of U.S. Publication No. 2012/0207697. 1,1,3,3-Tetramethyl-2,3,4,5-tetrahydro-1H-7,9-diaza-cyclopenta[a]naphthalene (Formula VIII) was prepared according to the disclosure of U.S. Publication No. 2012/0277325.

Example IV

The fragrance properties of the above compounds (i.e., Formulas III-VIII) were evaluated using (i) odor strength of 0 to 10, where 0=none, 1=very weak, 5=moderate, 10=extremely strong; and (ii) level of complexity, where 0=none, 1=very low, 5=moderate, 10=extremely high. Averaged scores are reported in the following:

| Chemical Name | Compound | Odor Profile | Strength | Complexity |
| --- | --- | --- | --- | --- |
| 7,7,8,9,9-Pentamethyl-8,9-dihydro-7H-cyclopenta[H]quinazoline (Formula III) | | Powerful and complex with warm, musky and sensual combination. Having a very bright top note supported by warm woody background and overall sweetness. As it dried down, the note was more apparent and complex with muskiness, woodiness and sweetness, which became the predominant features. | 9 | 9 |
| 6,7,8,9-Tetrahydro-7,7,9,9-pentamethyl-5H-cyclopenta[H]quinazoline (Formula VI) | | Having a musky note supported by an ambery feature, which provided additional strength and dimension. | 9 | 9 |
| 6,6a,7,8,9,9a-Hexahydro-7,7,9,9-pentamethyl-5H-cyclopenta[H]quinazoline (Formula VII) | | Having an ambery note supported by a musky feature, which was further supported by woody and creamy notes that added complexity. | 8 | 8 |
| 1,1,3,3-Tetramethyl-2,3,4,5-tetrahydro-1H-7,9-diaza-cyclopenta[a]naphthalene (Formula VIII) | | Having a musky note supported by a woody feature but less interesting, weak and not clean. | 4 | 4 |
| 7,7,8,9,9-Pentamethyl-6,6A,7,8,9,9A-hexahydro-5H-cyclopenta(F)quinazoline (Formula IV); and 6,6,7,8,8-Pentamethyl-5A,6,7,8,8A,9-hexahydro-5H-cyclopenta(G)quinazoline (Formula V) (1:1) | | Ambery, musky and fruity but weak without copmplexity. | 2 | 2 |

Formula III exhibited powerful, complex and desirable odors, which were however distinct from the odors of Formulas VI and VII and superior in strength and complexity to the odors of Formulas IV, V and VIII.

What is claimed is:

1. A compound of formula:

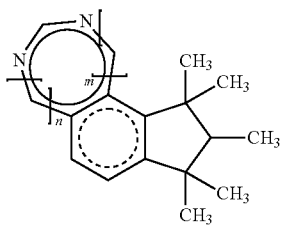

wherein m and n are integers of 0 or 1, with the proviso that when m is 0, n is 1 and when m is 1, n is 0; and wherein the dashed circle represents either single or double bonds.

2. The compound of claim 1, wherein the compound is 7,7,8,9,9-pentamethyl-8,9-dihydro-7H-cyclopenta[H]quinazoline.

3. The compound of claim 1, wherein the compound is 7,7,8,9,9-pentamethyl-6,6A,7,8,9,9A-hexahydro-5H-cyclopenta(F)quinazoline.

4. A fragrance formulation containing an olfactory acceptable amount of a compound of formula:

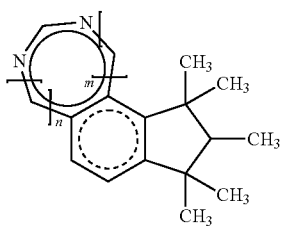

wherein m and n are integers of 0 or 1, with the proviso that when m is 0, n is 1 and when m is 1, n is 0; and wherein the dashed circle represents either single or double bonds.

5. The fragrance formulation of claim 4, wherein the compound is 7,7,8,9,9-pentamethyl-8,9-dihydro-7H-cyclopenta[H]quinazoline.

6. The fragrance formulation of claim 4, wherein the compound is 7,7,8,9,9-pentamethyl-6,6A,7,8,9,9A-hexahydro-5H-cyclopenta(F)quinazoline.

7. The fragrance formulation of claim 4, wherein the fragrance formulation further comprising a product selected from the group consisting of a perfume, a cologne, toilet water, a cosmetic product, a personal care product, a fabric care product, a cleaning product, and an air freshener.

8. The fragrance formulation of claim 7, wherein the cleaning product is selected from the group consisting of a detergent, a dishwashing composition, a scrubbing compound, and a window cleaner.

9. The fragrance formulation of claim 4, wherein the olfactory acceptable amount is from about 0.005 to about 50 weight percent of the fragrance formulation.

10. The fragrance formulation of claim 4, wherein the olfactory acceptable amount is from about 0.5 to about 25 weight percent of the fragrance formulation.

11. The fragrance formulation of claim 4, wherein the olfactory acceptable amount is from about 1 to about 10 weight percent of the fragrance formulation.

12. A method of improving, enhancing or modifying a fragrance formulation through the addition of an olfactory acceptable amount of a compound of formula:

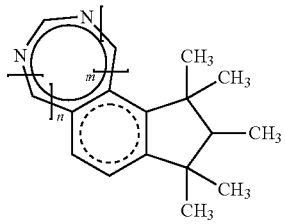

wherein m and n are integers of 0 or 1, with the proviso that when m is 0, n is 1 and when m is 1, n is 0; and wherein the dashed circle represents either single or double bonds.

13. The method of claim 12, wherein the compound is 7,7,8,9,9-pentamethyl-8,9-dihydro-7H-cyclopenta[H]quinazoline.

14. The method of claim 12, wherein the compound is 7,7,8,9,9-pentamethyl-6,6A,7,8,9,9A-hexahydro-5H-cyclopenta(F)quinazoline.

15. The method of claim 12, wherein the olfactory acceptable amount is from about 0.005 to about 50 weight percent of the fragrance formulation.

16. The method of claim 12, wherein the olfactory acceptable amount is from about 0.5 to about 25 weight percent of the fragrance formulation.

17. The method of claim 12, wherein the olfactory acceptable amount is from about 1 to about 10 weight percent of the fragrance formulation.

* * * * *